United States Patent [19]

Jung

[11] 4,407,758
[45] * Oct. 4, 1983

[54] DIALKYLZINC COMPOSITIONS HAVING IMPROVED THERMAL STABILITY

[75] Inventor: Alfred K. Jung, Queens, N.Y.

[73] Assignee: Stauffer Chemical Company, Westport, Conn.

[ * ] Notice: The portion of the term of this patent subsequent to Sep. 6, 2000 has been disclaimed.

[21] Appl. No.: 316,597

[22] Filed: Oct. 30, 1981

[51] Int. Cl.$^3$ .............................................. C07F 3/06
[52] U.S. Cl. .................................. 260/429.9; 502/150
[58] Field of Search ...................................... 260/429.9

[56] References Cited

U.S. PATENT DOCUMENTS

| | | | |
|---|---|---|---|
| 3,124,604 | 3/1964 | Hüther | 260/429.9 |
| 3,144,473 | 8/1964 | Boor et al. | 260/429.9 |
| 3,313,741 | 4/1967 | Uelzmann et al. | 260/429.9 X |
| 3,475,475 | 10/1969 | Eidt | 260/429.9 |
| 3,579,480 | 5/1971 | Overmars et al. | 260/429.9 X |
| 3,579,481 | 5/1971 | Overmars et al. | 260/429.9 X |
| 3,641,080 | 2/1972 | Radtke | 260/429.9 |
| 3,641,081 | 2/1972 | Radtke | 260/429.9 |

*Primary Examiner*—Helen M. S. Sweed
*Attorney, Agent, or Firm*—William C. Gerstenzang; Howard K. Kothe

[57] ABSTRACT

Acenaphthylene compounds are added to dialkylzinc compositions to improve the thermal stability of the compositions.

8 Claims, No Drawings

DIALKYLZINC COMPOSITIONS HAVING IMPROVED THERMAL STABILITY

BACKGROUND OF THE INVENTION

The present invention relates to dialkylzinc compositions having improved thermal stability. More particularly, the present invention relates to compositions comprising a dialkylzinc compound in admixture with a stabilizer which reduces the thermal decomposition rate of the dialkylzinc compound.

Dialkylzinc compounds, particularly diethylzinc, are known to be useful as polymerization catalysts in Ziegler-Natta type systems, as chemical intermediates as well as alkylating agents. In addition, diethylzinc has been found useful as a preservative for paper, which can be applied to existing books and the like to extend their useful life, as is reported in the October 1979 issue of "Chemical and Engineering News".

Unfortunately, however, the dialkylzinc compounds in addition to being pyrophoric and highly reactive with water, are thermally unstable and can decompose rapidly at elevated temperatures. The decomposition is exothermic, and could therefore become a "runaway reaction" unless special precautions are taken to prevent it. Thus, for example, a quantity of this material in storage could slowly increase in temperature, due to slow decomposition, until a point was reached where the decomposition rate increased to a level which could present a hazard.

It has been reported, for example, that the halflife of diethylzinc is 10 days at 120° C., about 1 day at 150° C. and only a few minutes at 200° C.

The thermal instability of these compounds has been a significant deterrent to their use because measures required to prevent the possibility of a runaway reaction sometimes outweigh the benefits to be achieved.

If, however, the dialkylzinc compounds could be stabilized against thermal decomposition so that their decomposition rates were more manageable, the use of these compounds would be far more attractive.

A need therefore exists for a method by which the thermal decomposition rates of diakylzinc compounds can be reduced.

It has now been found that the addition of acenapthylene compounds to dialkylzinc compounds substantially reduces their rates of thermal decomposition.

SUMMARY OF THE INVENTION

In accordance with the present invention there is provided a process for improving the thermal stability of a dialkylzinc compound represented by the formula R-Zn-R wherein R represents an alkyl radical having from 1 to about 8 carbon atoms which comprises adding to the dialkylzinc compound an acenapthylene compound represented by the formula

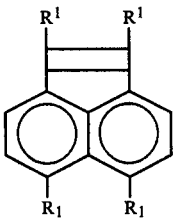

wherein each $R^1$ independently represents an alkyl radical, an olefin radical (conjugated with the aromatic moiety), an aryl radical or a substituted aryl radical, each having from 1 to about 12 carbon atoms, or hydrogen; in an amount sufficient to reduce the thermal decomposition rate of the dialkylzinc compound.

In accordance with another aspect of the present invention there is provided a dialkylzinc composition having improved stability against thermal decomposition comprising a dialkylzinc compound represented by the formula R-Zn-R wherein R represents an alkyl radical having from 1 to about 8 carbon atoms, in admixture with an acenaphthylene compound represented by the formula

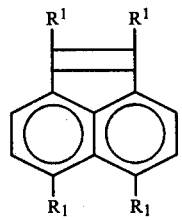

wherein each $R^1$ independently represents an alkyl radical, an olefin radical conjugated with the aromatic moiety, an aryl radical or substituted aryl radical, each having from 1 to about 12 carbon atoms, or hydrogen; said acenaphthylene compound being present in an amount sufficient to reduce the thermal decomposition rate of said dialkylzinc compound.

DETAILED DESCRIPTION OF THE INVENTION

More in detail the dialkylzinc compounds which are stabilized in accordance with the present invention are represented by the formula R-Zn-R wherein R represents an alkyl radical having from 1 to about 8 carbon atoms. These compounds include, but are not limited to dimethylzinc, diethylzinc, dibutylzinc, diisopropylzinc, and diisobutylzinc; although diethylzinc is preferred.

The acenaphthylene compounds which are used are represented by the formula

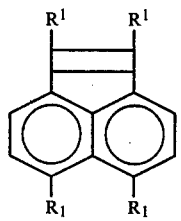

wherein each $R^1$ independently represents an alkyl radical, an olefin radical conjugated with the aromatic moiety, an aryl radical or a substituted aryl radical, each having from 1 to about 12 carbon atoms, or hydrogen. A particularly preferred acenaphthylene compound is acenaphthylene.

The acenaphthylene stabilizer can be added to the dialkylzinc by any conventional method, although the special handling requirements for the pyrophoric dialkylzinc compounds should be observed.

The amount of acenaphthylene compound which is added is an amount which is sufficient to achieve the desired degree of stabilization. When, for example, the dialkylzinc compound being stabilized is diethylzinc, and the acenaphthylene compound being used is acenaphthylene, effective amounts of acenaphthylene range from about 3% to about 5% by weight of diethylzinc.

The dialkylzinc compounds are shipped and used in industrial processes either neat, or diluted with hydrocarbon solvents. Hydrocarbon solutions of dialkylzinc compounds, particularly diethylzinc, typically range in concentrations from 5% up to 50% by weight. Solvents employed include, but are not limited to pentane, hexane, heptane, toluene and xylene. These solvents are, of course, dried before using because dialkylzinc compounds react with water.

The present invention may be practiced with either the neat dialkylzinc compound, or with the diluted forms.

In order that the present invention be more fully understood, the following examples are given by way of illustration. No specific details or enumerations contained therein should be construed as limitations except insofar as they appear in the appended claims. All parts and percentages are by weight unless otherwise specifically designated.

EXAMPLE I

A computer-controlled adiabatic calorimeter was used to determine the time required for the decomposition of diethylzinc to become a runaway reaction at various temperatures under adiabatic condition. The results are shown in Table I below.

TABLE I
TIME TO A RUNAWAY REACTION FOR THE ADIABATIC DECOMPOSITION OF DIETHYLZINC

| Temperature °C. | Time to a Runaway Reaction |
|---|---|
| 80 | 124.3 days |
| 90 | 33.6 days |
| 100 | 9.8 days |
| 110 | 3 days |
| 120 | 23.5 hours |
| 130 | 7.5 hours |
| 140 | 2.5 hours |

This demonstrates the thermal instability of diethylzinc.

EXAMPLE 2

Samples of diethylzinc were placed in a 300 ml. glass lined autoclave equipped with an internal thermocouple and pressure transducer. The autoclave was then equilibrated to room temperature, after which it was heated to increase the temperature of the contents at the rate of about 5° per minute. The temperature and pressure inside the autoclave were continuously measured. The results of this test are summarized in table II below.

TABLE II
SUMMARY OF DIETHYLZINC CONFINEMENT TESTS

| Wt. of Diethylzinc loaded (gms) | Exotherm* Initiation Temp. °C. | Maximum Temp. °C. | Maximum Pressure PSIG | Maximum Pressure ATM | Maximum Rate of Pressure Rise psi/sec | Maximum Rate of Pressure Rise ATM/sec. | Moles of Gas Generated per Mole of DEZ (1.) | Maximum Rate of Gas Generated moles/sec/mole |
|---|---|---|---|---|---|---|---|---|
| 15 | 248 | 285 | 680 | 47 | 270 | 18 | 2.4 | 1.01 |
| 60 | 207 | 423 | 2750 | 188 | 1435 | 98 | 1.7 | 1.02 |

*In one previous run, the start of rapid pressure rise occurred at 120° C.
(1.) DEZ: Diethylzinc This example shows that the thermal decomposition of diethylzinc in confinement can result in substantial pressure generation. It also shows that the rate of pressure rise is dependent on sample size, but that the moles of gas generated per second for each mole of diethylzinc is independent of sample size and is on the order of 1.01 moles gas/second/mole of diethylzinc.

EXAMPLE III

Using the same equipment and procedure as in Example II, samples of diethylzinc were tested both with and without the additives listed in Table III. The results of these tests are shown in Table III.

TABLE III
SUMMARY OF DIETHYLZINC CONFINEMENT TESTS

| Run | Wt. of Diethylzinc loaded gms | Additive | Exotherm initiation Temp. °C. | Maximum Temp. °C. | Maximum Pressure PSIG | Maximum Pressure ATM. |
|---|---|---|---|---|---|---|
| 1 | 15 | none | 248 | 285 | 680 | 47 |
| 2 | 60 | none | 207 | 423 | 2750 | 188 |
| 3 | 60 5% | Acenaphthylene | 200 | 413 | 940 | 65 |
| 4 | 68 ~ 5% | Acenaphthene | 208 | 499 | 1710 | 117 |
| 5 | 60 ~ 1% | Anthracene | 193 | 405 | >5000 | 341 |
| 6 | 23 ~ 3% | Anthracene | ~210 | 419 | 490 | 34 |
| 7 | 32 ~ 5% | Anthracene | 195 | 404 | 480 | 34 |
| 8 | 60 5% | Anthracene | 210 | 383 | 850 | 59 |

TABLE III-continued

SUMMARY OF DIETHYLZINC CONFINEMENT TESTS

| Run | Wt. of Diethylzinc loaded gms | Maximum Rate of Pressure Rise | | Moles of Gas generated per mole of Diethylzinc | Maximum Rate of Gas Generation Moles/sec/mole of Diethylzinc |
|---|---|---|---|---|---|
| | | psi/sec | ATM/sec | | |
| 1 | 15 | 270 | 18 | 2.4 | 1.01 |
| 2 | 60 | 1435 | 98 | 1.7 | 1.02 |
| 3 | 60 | 42 | 3 | 0.58 | $3.1 \times 10^{-2}$ |
| 4 | 68 | 293 | 20 | 0.83 | 0.176 |
| 5 | 60 | 1995 | 136 | >3.2 | 1.42 |
| 6 | 23 | ~5 | 0.3 | 0.9 | $1.1 \times 10^{-2}$ |
| 7 | 32 | 4.3 | 0.3 | 0.6 | $6.5 \times 10^{-3}$ |
| 8 | 60 | 16 | 1.0 | 0.55 | $1.2 \times 10^{-2}$ |

This example demonstrates that the addition of 5% acenaphthylene to the diethylzinc reduces the gas generation rate by a factor of about 30.

It will thus be seen that the process and composition set forth have desirable advantages over the prior art. Since certain changes may be made in the process and composition without departing from the scope of the invention, it is intended that all matter contained in the above description shall be interpreted as illustrative and not in a limiting sense.

I claim:

1. A dialkylzinc composition having improved stability against thermal decomposition comprising a dialkylzinc compound represented by the formula

wherein R represents an alkyl radical having from 1 to about 8 carbon atoms, in admixture with an acenaphthylene compound represented by the formula

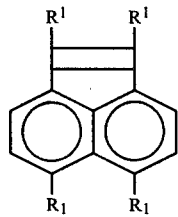

wherein each $R^1$ independently represents an alkyl radical, an olefin radical conjugated with the aromatic moiety, an aryl radical or a substituted aryl radical, each having from 1 to about 12 carbon atoms, or hydrogen; said acenaphthylene compound being present in an amount sufficient to reduce the thermal decomposition rate of said dialkylzinc compound.

2. The dialkylzinc composition of claim 1 wherein R represents an ethyl radical and said dialkylzinc compound is diethylzinc.

3. The dialkylzinc composition of claim 2 wherein said acenaphthylene compound is acenaphthylene.

4. The dialkylzinc composition of claim 3 wherein said acenaphthylene is present in an amount ranging from about 3% to about 5% based on the weight of dialkylzinc compound present.

5. A process for improving the thermal stability of a dialkylzinc compound represented by the formula

wherein R represents an alkyl radical having from 1 to about 8 carbon atoms which comprises adding to said dialkylzinc compound an acenapthylene compound represented by the formula

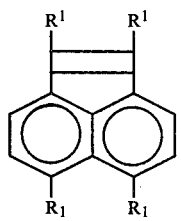

wherein each $R^1$ independently represents an alkyl radical, an olefin radical conjugated with the aromatic moiety, an aryl radical or a substituted aryl radical, each having from 1 to about 12 carbon atoms, or hydrogen; in an amount sufficient to reduce the thermal decomposition rate of said dialkylzinc compound.

6. The process of claim 5 wherein R represents an ethyl radical and said dialkylzinc compound is diethylzinc.

7. The process of claim 6 wherein said acenaphthylene compound is acenaphthylene.

8. The process of claim 7 wherein said acenaphthylene compound is present in an amount ranging from about 3% to about 5% based on the weight of dialkylzinc present.

* * * * *